United States Patent [19]

Yang et al.

[11] Patent Number: 5,486,624
[45] Date of Patent: Jan. 23, 1996

[54] KOJIC ACID DERIVATIVE

[75] Inventors: Chang M. Yang, Seongnam; Jong Y. Hong; Ki W. Lee, both of Seoul; Byeong G. Lee, Suwon; Dong I. Chang, Anyang, all of Rep. of Korea

[73] Assignee: Pacific Corporation, Seoul, Rep. of Korea

[21] Appl. No.: 374,914

[22] Filed: Jan. 19, 1995

[30] Foreign Application Priority Data

Feb. 1, 1994 [KR] Rep. of Korea .................... 1994-1795

[51] Int. Cl.$^6$ ................................................. C07D 309/40
[52] U.S. Cl. ............................................... 549/418
[58] Field of Search ............................................ 549/418

[56] References Cited

FOREIGN PATENT DOCUMENTS

| | | |
|---|---|---|
| 54-92632 | 7/1979 | Japan . |
| 56-18569 | 4/1981 | Japan . |
| 56-77272 | 6/1981 | Japan . |
| 60-9722 | 4/1985 | Japan . |
| 60-7961 | 12/1985 | Japan . |
| 62-3820 | 11/1987 | Japan . |
| 1-121205 | 5/1989 | Japan . |
| 64-83008 | 6/1989 | Japan . |
| 2-28105 | 4/1990 | Japan . |
| 3-14508 | 2/1991 | Japan . |
| 4-187618 | 7/1992 | Japan . |
| 4-145096 | 8/1992 | Japan . |
| 5-39298 | 6/1993 | Japan . |

*Primary Examiner*—Marianne M. Cintins
*Assistant Examiner*—Phyllis G. Spivack
*Attorney, Agent, or Firm*—Nixon & Vanderhye

[57] ABSTRACT

Kojic acid derivatives of the following formula (I)

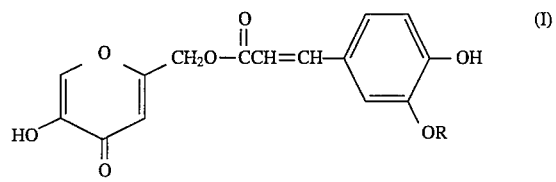

where R is a hydrogen atom or methyl group, as radical scavengers and strong inhibitors of tyrosinase, an enzyme involved in a melanin formation.

1 Claim, No Drawings

KOJIC ACID DERIVATIVE

BACKGROUND OF THE INVENTION

1. Field of the Invention

The present invention relates to novel kojic acid derivatives, and more particularly it relates to novel kojic acids substituted at the 2-position with 3,4-dihydroxycinnamic acid or 4-hydroxy-3-methoxycinnamic acid. These derivatives exhibit a strong skin whitening activity.

2. Description of Prior Art

Kojic acid, which is obtained from culturing Aspergillus, strongly inhibits the action of tyrosinase, an enzyme involved in the formation of melanin, which is a major factor in determining the color of human skin. It has been reported that kojic acids inhibit the activity of tyrosinase by forming a chelate with the copper ion in the tyrosinase through the 5-hydroxyl and 4-carbonyl groups. Based on this tyrosinase-inhibiting activity of kojic acid, various cosmetic compositions have been proposed containing kojic acid as an active ingredient(See JP 56-18569B).

Further, JP 54-92632A, JP 56-77272A, JP 60-7961B and JP 60-9722B disclose methods for improving the properties of kojic acid, such as storage stability, compatibility, solubility, and the like, and various kojic acid derivatives such as kojic mono- or di-fatty acid esters, having an improved activity of inhibiting tyrosinase. Moreover, JP 3-14508A, JP 4-145096A, JP 4-187618A and JP 5-39298A propose various kojic acid derivatives having a strong tyrosinase-inhibiting activity, such as kojic ethers, glucosylated kojic acids and amino-protected amino acid kojic acids. Furthermore, JP 62-3820B, JP 64-83008A, JP 1-121205A and JP 2-028105A disclose compositions incorporating various additives to improve the solubility of kojic acid and to enhance the skin-whitening activity.

The present inventors have discovered novel kojic acid derivatives having an improved tyrosinase-inhibiting activity as well as decreased side effects to human skin. They have found certain kojic acid derivatives of which the 2-hydroxymethyl group substituted with mono- or di-hydroxycinnamic acid show a superior tyrosinase inhibiting activity. Particularly, 2-dihydroxy cinnamoyl kojic acid exhibits an excellent activity to scavenge radicals, which are known to cause skin aging, and also exhibits decreased side effects to the skin.

SUMMARY OF THE INVENTION

Therefore, an object of the invention is to provide novel kojic acid derivatives having the following formula (I):

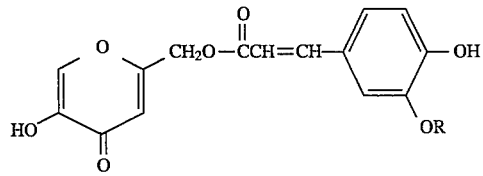

wherein, R is a hydrogen atom or methyl group.

DETAILED DESCRIPTION OF THE INVENTION

The kojic acid derivatives (I) of the present invention may be prepared by the process shown in the following reaction scheme:

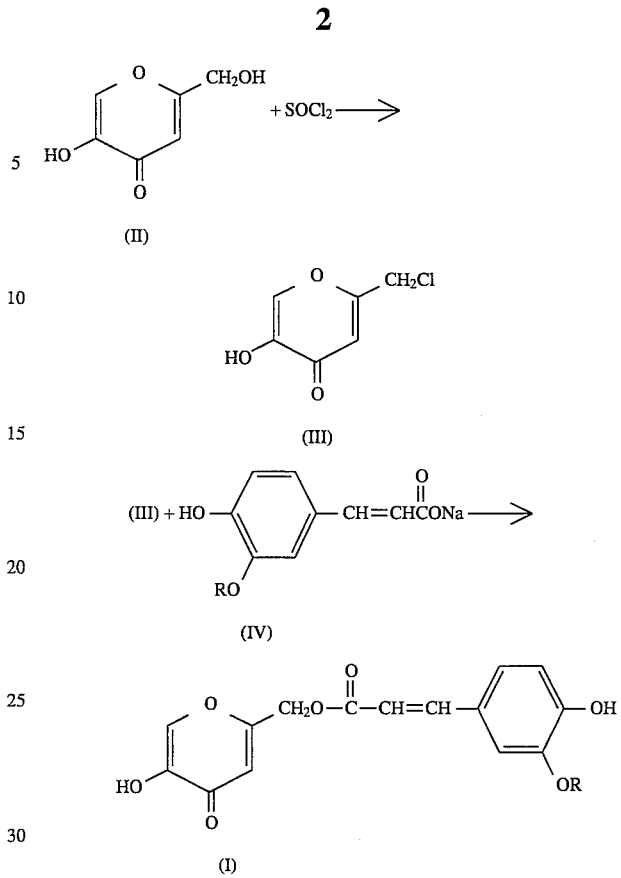

wherein, R has the same meaning defined as above.

The compounds of the formula (IV) may include, for example, sodium salts of 3,4-dihydroxycinnamic acid and of 4-hydroxy-3-methoxycinnamic acid.

The compounds of the formula (I) may include but are not limited to, 2-(3,4-dihydroxycinnamoyl)oxymethyl-5-hydroxy-4H-pyran-4-one and 2-(4-hydroxy-3-methoxy cinnamoyl) oxymethyl-5-hydroxy-4H-pyran-4-one.

The novel kojic acid derivatives of the formula (I) according to the present invention may be prepared, as shown in the above reaction scheme, by reacting kojic acid of the formula (II) with thionyl chloride(SOC12) in a solvent such as chloroform to give 2-chloromethyl-5-hydroxy-4H-pyran-4-one("Chlorokojic acid") of the formula (III) and reacting the compound of the formula (IV) with the chlorokojic acid in a solvent such as N,N-dimethylformamide to give the present compound (I).

The compound of the formula (I) according to the present invention is a kojic acid derivative in which the 2-hydroxymethyl group is substituted with hydroxycinnamic acid; it exhibits a 20 fold higher activity than that of known kojic acid derivatives in terms of $IC_{50}$ (Concentration of kojic acid to inhibit the enzyme activity by 50%)(See Experimental Example 1 below). Particularly, kojic acid substituted at the 2-position with dihydroxycinnamic acid, for example 3,4-dihydroxy cinnamic acid, is capable of strongly inhibiting tyrosinase as well as can effectively scavenging harmful radicals.

In general, radicals formed in the living body are known to cause a skin aging and a radical-scavenger can retard the skin aging(Japan Fragrance Journal, June, 1990, pp 39–46). Known scavengers of harmful radicals in the living body include the anti-oxidants, vitamin E(tocopherol), hydroquinone, and superoxide dismutase(SOD). The 2-dihydroxycinnamic acid substituted kojic acids (I) show an equivalent activity to that of these known scavengers (See Experimental Example 2).

Further, it has been confirmed that the present compounds (I) have only slight said effects on human skin as demonstrated in a skin safety experiment(Experimental Example 3).

Accordingly, the present compounds (I) can be incorporated into cosmetic compositions or topical dermatological medicaments for whitening the skin, preventing skin tanning or pigmentation.

The present invention will be illustrated hereinafter in more detail by way of non-limiting Examples. Examples 1 and 2 show the preparation and identification of the compounds (I); Experimental Example 1 compares the tyrosinase-inhibiting activity of the compounds (I) and of kojic acid; Experimental Example 2 compares the radical-scavenging activity of the compounds (I) and of conventional anti-oxidants; and Experimental Example 3 shows a skin safety test of these compounds (I).

The method of preparing the intermediate compound (II) is illustrated in Reference Example.

Reference Example: Preparation of 2-chloromethyl-5-hydroxy-4H-pyran-4-one ("Chlorokojic acid")

50 g(351.8 mmol) of kojic acid was dissolved in 250 ml of N,N-dimethylformamide. The resulting solution was cooled in an ice bath of 10° C. and 30 ml(411.3 mmol) of thionyl chloride was added dropwise thereto. The mixture was stirred at room temperature for 2 hours and 2000 ml of ice water was added. The precipitate was filtered and dissolved into 1000 ml of ethyl acetate. The reaction product was dried over magnesium sulfate, decolored with active charcoal and filtered. The filtrate was concentrated and hexane was added to give crystals, which were then dried under vacuum to give 37.5 g(66.83%) of the desired chlorokojic acid as a yellow solid.

mp. : 165°–166° C. TLC (in hexane: ethyl acetate=1:2) Rf=0.5

Example 1: Preparation of 2-(3,4-dihydroxycinnamoyl)oxymethyl-5-hydroxy-4H-pyran-4-one 0.81 g(4.5 mmol) of 3,4-dihydroxycinnamic acid and 0.18 g (4.5 mmol) of sodium hydroxide were dissolved into 40 ml of methanol. Residues obtained after distillating in methanol dissolved into 70 ml of N,N-dimethylformamide and 0.65 g (4.05 mmol) of chlorokojic acid prepared in the Reference Example was added thereto. The resulting mixture was heated with stirring for 2 hours in an oil bath of 110° C. After distillating the solvent, the residue was dissolved in 300 ml of ethyl acetate. The ethyl acetate solution was washed with 5% hydrochloric acid and distilled water, dried over magnesium sulfate, decolored with active charcoal and filtered. The filtrate was concentrated to give 0.66 g(48.8%) of 2-(3,4-dihydroxycinnamoyl) oxymethyl-5-hydroxy-4H-pyran-4-one as a solid.

mp.: 186°–189° C. TLC (in acetic acid: ethyl ether=25:1) Rf=0.35 IR(KBr Pellet) : 3421, 1686, 1652 cm$^{-1}$ $^1$H-NMR(DMSO-d$_6$, δ) : 5.05(s, 2H), 6.34(d, 1H), 6.49(s, 1H) 6.74–7.17 (m, 3H), 7.56 (d, 1H), 8.10 (s, 1H) 9.15 (s, 1H), 9.23 (s, 1H), 9.66 (s, 1H)

Example 2 : Preparation of 2-(4-hydroxy-3-methoxycinnamoyl) oxymethyl-5-hydroxy-4H-pyran-4-one 0.87 g(4.5 mmol) of 4-hydroxy-3-methoxycinnamic acid and 0.18 g (4.5 mmol) of sodium hydroxide were dissolved into 40 ml of methanol. Residue obtained after distillating methanol was dissolved in 70 ml of N,N-dimethylformamide and 0.65 g (4.05 mmol) of chlorokojic acid prepared in the Reference Example was added thereto. The resulting mixture was heated with stirring for 2 hours in an oil bath of 110° C. After distillating the solvent, the residue was dissolved in 300 ml of ethyl acetate. The ethyl acetate solution was washed with 5% hydrochloric acid and distilled water, dried over magnesium sulfate, decolored with active charcoal and filtered. The filtrate was concentrated to give 0.6g(41.9%) of 2-(4-hydroxy-3-methoxy cinnamoyl)oxymethyl-5-hydroxy-4H-pyran-4-one as a solid.

mp. : 182°–183° C., TLC (in acetic acid: ethyl ether=25:1) Rf=0.45 IR(KBr Pellet) : 3474, 1711, 1649 cm$^{-1}$ $^1$H-NMR(DMSO-d$_6$, δ) : 3.81(s, 3H), 5.06(s, 2H), 6.51(s, 1H) 6.56)d, 1H), 7.12–7.36(m, 3H) 7.63(d, 1H), 8.10(s, 1H), 9.25(s, 1H) 9.66 (s, 1H)

In order to examine the tyrosinase-inhibiting activity, harmful radical-scavenging activity and skin safety of the present kojic acid derivatives, the following tests were carried out using the compounds of Examples 1 and 2.

Experimental Example 1 : Tyrosinase-inhibiting activity

Tyrosinase-inhibiting activity of the compounds of Examples 1 and 2 were compared with that of kojic acid as follows:

<Method>

Tyrosinase, which was extracted from mushroom, was purchased from SIGMA. Tyrosine and a substrate were dissolved in distilled water at a concentration of 0.3 mg/ml and 1.0 ml of the resulting solution was placed into a test tube. 1.0 ml of potassium sulfate buffer(0.1M, pH6.8), 0.9 ml of stepwise dilutions of compounds of Examples 1 and 2 or kojic acid were added thereto. The resulting mixture was reacted at 37° C. in an incubator for 10 minutes. Ethanol and water were used to dilute the test compounds. As a control, 0.9 ml of a 1:1 mixture of ethanol and water was used.

0.1 ml of tyrosine solution (2,500 unit/ml) was added and the reaction mixture was reacted at 37° C. in an incubator for 10 minutes. The test tube was quickly cooled in an ice water bath to stop the reaction, and absorbance was measured at 475 nm. The tyrosinase-inhibiting activities of the compounds of Examples 1 and 2 and kojic acid were calculated by the following equation:

$$\text{Inhibition of tyrosinase (\%)} = 100 - \frac{\text{Absorbance of test compound}}{\text{Absorbance of control}} \times 100$$

IC$_{50}$, i.e., the concentration of test compound which inhibits tyrosinase by 50% was calculated by serial dilution for each test compound.

<Results>

The results are shown in Table 1.

TABLE 1

| Test Compounds | IC$_{50}$ (μM) |
| --- | --- |
| Kojic acid | 80 |
| Compound in Example 1 | 4 |
| Compound in Example 2 | 4 |

As can be seen from the results in Table 1, the compounds of Examples 1 and 2 show a 20 fold higher activity of tyrosinase inhibition than that of kojic acid.

Experimental Example 2: Radical-scavenging activity

Harmful radical-scavenging activities of the compounds of Examples 1 and 2 were compared with those of conventional anti-oxidants using a DPPH (diphenylpicrylhydrazyl) radical-scavenging test as follows:

<Method>

DPPH was dissolved into ethanol to a concentration of 100 μM. A series of dilutions of compounds of Examples 1 and 2, vitamin C, vitamin E or hydroquinone were prepared. Ethanol and water were used to dilute the test compounds. As a control, a 1:1 mixture of ethanol and water was used. The series of dilutions of each test compound were mixed with 1,900 μl of DPPH solution and the dilution solvent was added to 2.0 ml. The resulting mixture was reacted in an incubator at 37° C. for 30 minutes. Absorbance was measured at 515 nm. The radical-scavenging activities of the compounds of Examples 1 and 2 and conventional anti-oxidants were calculated by the following equation:

$$\text{Radical scavenging activity (\%)} = 100 - \frac{\text{Absorbance of test compound}}{\text{Absorbance of control}} \times 100$$

$IC_{50}$, i.e., the concentration of test compound which scavenge the radical, DPPH by 50% was calculated by the serial dilution method for each test compound.

<Results>

The results are shown in Table 2.

TABLE 2

| Test Compounds | $IC_{50}$ |
|---|---|
| Compound in Example 1 | 12.3 μM |
| Compound in Example 2 | 70.0 μM |
| Vitamin C | 29.2 μM |
| Vitamin E | 34.8 μM |
| Hydroquinone | 25.4 μM |

As can be seen from the results in Table 2, the compound of Example 1, i.e., 2-(3,4-dihydroxycinnamoyl)-substituted kojic acid showed a strong activity as a radical scavenger.

Experimental Example 3: Safety in the living body

In order to examine the safety of the compounds of Examples 1 and 2, a human body patch test was carried out as follows:

<Method>

The brachium of thirty(30) healthy volunteers (15 females and 15 males) was thoroughly washed with 70% ethanol and applied with a plaster containing 20 μl of a conventional creamy preparation incorporating 0.2 wt. % of one of the compounds of Examples 1 and 2. The plaster was thoroughly bonded to the brachium using an adhesive tape. 48 hours later, the tape and chamber were removed, and the adherent site of the arm was wiped with a gauze to remove any remaining preparation. The site was observed for redness(erythma), swelling, and papuol. 48 hours later, the site was examined again.

<Results>

The results are shown in Table 3.

TABLE 3

| Test Preparations | 48 hours later | 96 hours later |
|---|---|---|
| Control | 0/30 | 0/30 |
| Containing Compd in Ex. 1 | 1/30 | 0/30 |
| Containing Compd in Ex. 2 | 1/30 | 0/30 |

The results are shown in terms of the number of positive subjects/the number of total subjects.

As can be seen from the results in Table 3, although the preparations containing the compounds of Examples 1 and 2 show a weak positive response after 48 hours, these responses disappeared after 96 hours. Accordingly, the compounds of Examples 1 and 2 are safe to human skin.

What is claimed is:

1. A kojic acid derivative represented by the formula (I):

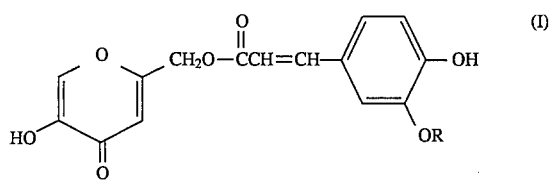

wherein, R is a hydrogen atom or methyl group.

* * * * *